United States Patent
Reutrakul et al.

(10) Patent No.: US 6,403,636 B1
(45) Date of Patent: Jun. 11, 2002

(54) XANTHONE COMPOUNDS, THEIR PREPARATION AND USE AS MEDICAMENT

(75) Inventors: Vichai Reutrakul; Thaiwatchai Santisuk, both of Bangkok (TH); Gerhard Noessner, Offenbach (DE); Juergen Schmidt, Uhldingen Muehlhofen (DE); Bernd Nickel, Muehltal (DE); Thomas Klenner, Ingelheim (DE); Sebastian Hose, Wuerzburg (DE)

(73) Assignee: Zentaris AG, Frankfurt am Main (DE)

( * ) Notice: Subject to any disclaimer, the term of this patent is extended or adjusted under 35 U.S.C. 154(b) by 0 days.

(21) Appl. No.: 09/605,650

(22) Filed: Jun. 28, 2000

(30) Foreign Application Priority Data

Jul. 1, 1999 (EP) ............................................. 99112553

(51) Int. Cl.[7] ................... A61K 31/352; C07D 493/18; A61P 43/00

(52) U.S. Cl. ........................ 514/453; 549/381; 549/414
(58) Field of Search ................................ 549/381, 382, 549/414; 514/453

(56) References Cited

PUBLICATIONS

Thoison, et al, 2000, J. Nat. Prod., 63(40), 441–446.*

* cited by examiner

*Primary Examiner*—Floyd D. Higel
*Assistant Examiner*—Andrea D'Souza Small
(74) *Attorney, Agent, or Firm*—Pillsbury Winthrop LLP

(57) ABSTRACT

This invention relates to novel xanthone compounds, their preparation and use as medicament. More particularly this invention is directed to the isolation of the novel xanthone natural product sootepenseone from *Dasymaschalon sootepense* Craib, Annonaceae, its identification and derivatization, and the use of sootepenseone and its derivatives as anticancer agents.

10 Claims, No Drawings

XANTHONE COMPOUNDS, THEIR PREPARATION AND USE AS MEDICAMENT

INTRODUCTION

This invention relates to novel xanthone compounds, their preparation and use as a medicament. More particularly this invention is directed to the isolation of the novel xanthone natural product sootepenseone from *Dasymaschalon sootepense* Craib, Annonaceae, its identification and derivatization, and the use of sootepenseone and its derivatives as anticancer agents.

FIELD OF INVENTION

Cancer is perhaps one of the most active anti-human factor operating in the world today, and efforts are being made all over the scientific world to prevent and eradicate it.

New agents with chemotherapeutic value in the fight against cancer is obviously a medical problem of high importance. But the development of new drugs in the cancer field is a difficult task given that anticancer agents must be lethal to, or incapacitate tumor cells, but they should not cause excessive damage to normal cells. At present the state of knowledge in cancer biology and in medical chemistry does not warrant the designing of new classes of molecules which may be effective antitumor agents. Despite the great progress made in cancer biology, molecular pharmacology, pharmacokinetics, medical chemistry and allied fields, the knowledge sought after, is still elusive.

Since the concept of chemotherapeutic treatment of malignant diseases had come to the forefront during the last decades, plant principles and their derivatives have been intensively investigated by scientists all over the world as new antitumor inhibitors. Examples for important anticancer agents of plant origins are the alkaloids vincaleukoblastine (vinblastine) and leurocristine (vincristine), both isolated from *Catharanthus roseus*. A comprehensive review on natural products as anticancer agents is given by Shradha Sinha and Audha Jain, in: Progess in Drug Research, Vol. 42, pages 53–132 (1994) Basel (Switzerland).

SUMMARY OF INVENTION

In accordance with the present invention there are provided novel cytotoxic xanthone compounds of the general formula (I)

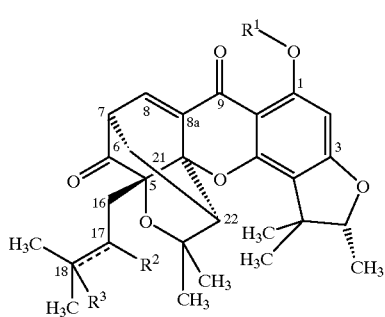

(I)

wherein $R^1$ is a hydrogen atom; a methyl group (—$CH_3$), a $C_2$–$C_6$ alkyl residue, a formyl group (—CHO); an acetyl residue (—$COCH_3$), —CO—$C_{2-6}$-alkyl, CO—$C_{3-8}$-cycloalkyl, —CO—$C_{6-18}$-aryl or —CO—$C_{7-24}$-aralkyl residue each having optionally one or more substituents selected from the group consisting of —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl)($C_{6-14}$-aryl), —$NHCOR^2$, —$NO_2$, —CN, —(CO)$R^3$, —(CS)$R^4$, —F, —CI, —Br, —I, —O—$C_{1-6}$-alkyl, —O—$C_{6-14}$-aryl, —O—(CO)$R^5$, —S—$C_{1-6}$-alkyl, —S—$C_{6-14}$-aryl, —$SOR^6$, and —$SO2R^7$, wherein $R^2$ to $R^7$ stands independently of each other for a hydrogen atom, —$C_{1-6}$-alkyl, —O—$C_{1-6}$-alkyl, —O—$C_{6-14}$-aryl, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl)($C_{6-14}$-aryl), —S—$C_{1-6}$-alkyl, —S—$C_{6-14}$-aryl residue;

a —COO—$C_{1-6}$-alkyl residue having optionally one or more substituents selected from the group consisting of —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl)($C_{6-14}$-aryl), —$NHCOR^8$, —$NO_2$, —CN, —(CO)$R^9$, —(CS)$R^{10}$, —F, —CI, —Br, —I, —O—$C_{1-6}$-alkyl, —O—$C_{6-14}$-aryl, —O—(CO)$R^{11}$, —S—$C_{1-6}$-alkyl, —S—$C_{6-14}$-aryl, —$SOR^{12}$, and —$SO2R^{13}$, wherein $R^8$ to $R^{13}$ stands independently of each other for a hydrogen atom, —$C_{1-6}$-alkyl, —O—$C_{1-6}$-alkyl, —O—$C_{6-14}$-aryl, —NH2, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl)($C_{6-14}$-aryl) ($C_{6-14}$-aryl) —S—$C_{1-6}$-alkyl, —S—$C_{6-14}$-aryl residue;

a —$CONR^{14}R^{15}$ residue wherein $R^{14}$ and $R^{15}$ stand independently of each other for a hydrogen atom, —$C_{1-6}$-alkyl, —O—$C_{1-6}$-alkyl, —O—$C_{6-14}$-aryl, —NH2, —$NHC_{1-6}$-alkyl, $N(C_{1-6}$-alkyl$)_2$, —$NHC_{6-14}$-aryl, —$N(C_{6-14}$-aryl$)_2$, —$N(C_{1-6}$-alkyl)($C_{6-14}$-aryl), —S—$C_{6-14}$-aryl residue;

or a counter cation selected from the group consisting of an alkali or earth alkali metal such as Li, Na, K, Ca, Mg, $NR^{16}R^{17}R^{18}R^{19}(+)$ wherein $R^{16}$ to $R^{19}$ stands independently of each other for a hydrogen atom or a $C_1$–$C_6$-alkyl residue;

$R^2$ and $R^3$ either form part of the $C^{17}$=$C^{18}$ -double bond or are each hydrogen, or a tautomer, an enantiomer, an stereoisomer or a physiologically acceptable salt or a solvate thereof or mixtures thereof.

In the case of a compound according to formula 1 above in the form of a phenolate with a di- or multivalent counter cation, the remaining positive charge can be compensated by association with a physiologically acceptable anion such as CI- or OH-.

The novel compound according to formula I, wherein $R^1$ is a hydrogen atom and $R^2$ and R3 form part of the $C^{17}$–$C^{18}$ -double bound, has been given the name sootepenseone (1).

According to another aspect of the invention there is provided a process for manufacturing a compound according to formula I by isolation of sootepenseone (1) from the leaves of *Dasymaschalon sootepenseone* Craib, Annonaceae and its subsequent derivatization.

The present invention further provides the use of the compounds according to formula (I) as medicament, in particular for the treatment of cancer diseases.

The present invention further provides pharmaceutical formulations, comprising an effective amount of a compound according to formula (I) for treating a patient in need thereof. As used herein, an effective amount of a compound according to formula (I) is defined as the amount of the compound which, upon administration to a patient, inhibits growth of tumor cells, kills malignant cells, reduces the volume or size of the tumors or eliminates the tumor entirely in the treated patient.

Thus, the substantially pure compounds in accordance with the invention can be formulated into dosage forms using pharmaceutically acceptable carriers for oral, topical or parenteral administration to patients in need of oncolytic therapy.

In a preferred embodiment, the patient is a mammal, in particular a human.

The effective amount to be administered to a patient is typically based on body surface area, patient weight, and patient condition. The interrelationship of dosages for animals or humans (based on milligrams per meter squared of body surface) is described by Freireich, E. J. et al., Cancer Chemother. Rep., 50 (4) 219 (1966). Body surface area may be approximately determined from patient height and weight (see e.g. Scientific Tables, Geigy Pharmaceuticals, Ardly, N.Y., pages 537–538 (1970)). Preferred dose levels will also depend on the attending physicians assessment of both the nature of the patient's particular cancerous condition and the overall physical condition of the patient. Effective antitumor doses of the present xanthone compounds range from 1 microgram per kilogram to about 5000 micrograms per kilogram of patient body weightmilligram, more preferably between 2 micrograms to about 1000 micrograms per kilogram of patient body weight.

Effective doses will also vary, as recognized by those skilled in the art, dependent on route of administration, excipient usage and the posibility of co-usage with other therapeutic treatments including other anti-tumor agents, and radiation therapy.

The present pharmaceutical formulation may be administered intravenous, intramuscular, intradermal, subcutaneous, intraperitoneally, topical, or intravenous in the form of a liposome.

Examples of dosage forms include aqueous solutions of the active agent, in an isotonic saline, 5% glucose or other well-known pharmaceutically acceptable liquid carrier. Additional solubilizing agents well-known to those familiar with the art can be utilized as pharmaceutical excipients for delivery of the active agent. Alternatively, the present compounds can be chemically modified to enhance water solubility, for example, by formation of pharmaceutically acceptable phenolate salts.

The present compounds can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active agent and solid carriers, and lubricants well-known to those familiar with the art. Examples of solid carriers include starch, sugar, bentonite. The compounds of the present invention can also be administered in a form of a hard shell tablet or capsule containing for example, lactose or mannitol as a binder and a conventional fillers and tableting agents.

The terms "effective amount" and "effective dose" as referring to the treatment of animals is defined herein to mean those quantities of alkaloid which will cause remession or inhibition of growth of the cancer disease in the animal to which it is administered, without imparting an untolerable toxic response. The effective amount may vary with the way of administration, the administration schedule, the kind of tumor, and other related factors, all of which may be varied without departing from the scope or operativeness of the invention. Generally an effective dose would be one within the range of about 0.001–100.0 mg/kg of body weight/day.

The terms "cancer" or "tumor" as used herein include, but are in no way limited to, adrenocarcinomas, glioblastomas (and other brain tumors), breast, cervical, colorectal, endometrial, gastric, liver, lung (small cell and non-small cell), lymphomas (including non-hodgkin's, Burkitt's, diffuse large cell, follicular and diffuse Hodgkin's), melanoma (metastatic), neuroblastoma, osteogenic sarcoma, ovarian, retinoblastoma, soft tissue sarcomas, testicular and other tumors which respond to chemotherapy.

Other objects and advantages of the invention will become readily apparent from the ensuing description.

DETAILED DESCRIPTION OF THE INVENTION

The inventive compounds according to formula (I) have a pentacyclic xanthone ring system (see for a review: Sultanbawa, M.U.S., Xanthonoids of tropical plants, Tetrahedron 36 (1980) 1465–1506). The following natural compounds are reported as having a similar ring system:

Gambogic acid (2), isolated from Garcinia hanburyi (see Amorosa, M. et al., Ann. Chim. (Rome), 1966, 56, 232; Ahmad, A. S. et al., J. Chem. Soc. (C), 1966, 772 (structure); Arnone, A. et al., Tetr. Lett., 1967, 4201 (pmr data, structure), morellin (3) isolated from Garcinia morella (see: Rao, B. S., J. Chem. Soc, 1937, 853 (isolation); Kartha, G. et al., Tetr. Lett., 1963, 459 (cryst. structure)); Nair, P. M. et al., Indian J. Chem., 1964, 2, 402 (structure)), hanburin (4) isolated from *Garcinia hanburyi* (see: Asano, J. et al., Phytochemistry, 1996, 41, 815 (isolation, uv, ir, pmr, cmr data) and forbesione (5) isolated from *Garcinia forbesii* (see: Yuan-Wah eong, Leslie J. Harrison, Graham J. Bennett and Hugh T.-W. Tan, J. Chem. Research (S) 1996, 392–393).

These compounds have at C-5 an isoprenyl side chain in common with a hydrogen bonded phenolic hydroxy group. Morellin (3) and gambogic acid (2) have a chromene ring system in common. All compounds (2) to (5) have in common a bicyclo[2.2.2]octene carbon skeleton fused to a 2,2-dimethyl-tetrahydrofuran ring system (see FIG. 1).

However, these compounds show significant structural differences as compared to the compounds according to formula I of the present invention:

1.) the C-5 isoprenyl side chain is oxidized to an aldehyde as in (3) or to a carboxyclic acid as in (2);
2.) the condensed dihydrofuran ring in 3,4-position is missing as in (4) or instead a pyranone ring is present in the 2,3-position as in (3)
3.) the ring system is substituted with an additional isoprenyl side chain at C-5 as in (3) and (5)

By contrast, the compounds of the present invention contain fully substituted dihydrofuran rings except at carbon 2', fused to the modified xanthone ring system.

For the taxonomy of *Dasymaschalon sootepense* Craib see V. H. Heywood, "Flowering Plants of the World", University Press, Oxford, 1978.

Surprisingly, the compounds of the present invention show remarkable antitumor activity. Moreover, the present compounds have a low toxicity.

Thus the xanthone compounds according to the present invention are new and involve an inventive step.

The structures of (2) to (5) are summarized below:

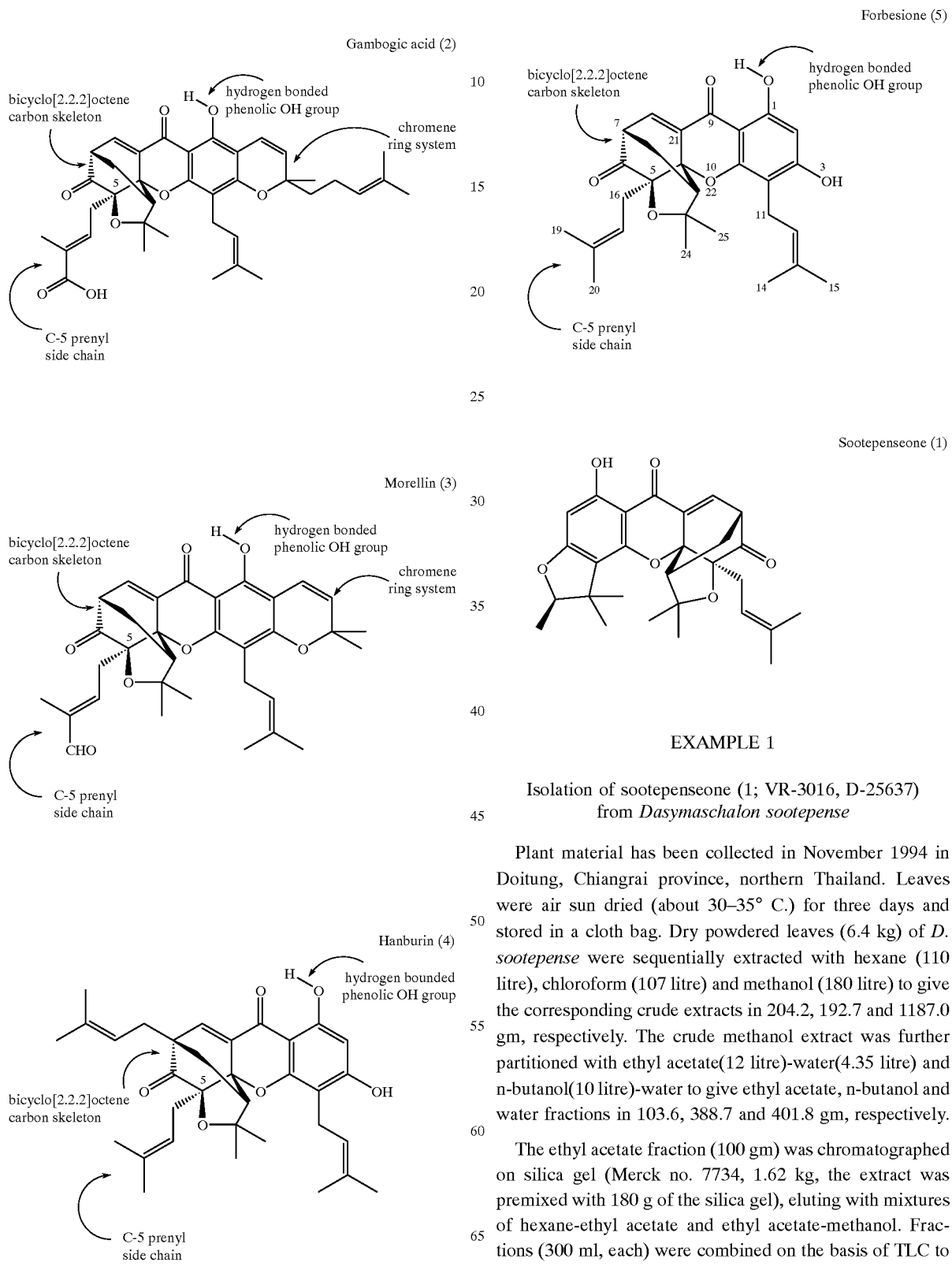

EXAMPLE 1

Isolation of sootepenseone (1; VR-3016, D-25637) from *Dasymaschalon sootepense*

Plant material has been collected in November 1994 in Doitung, Chiangrai province, northern Thailand. Leaves were air sun dried (about 30–35° C.) for three days and stored in a cloth bag. Dry powdered leaves (6.4 kg) of *D. sootepense* were sequentially extracted with hexane (110 litre), chloroform (107 litre) and methanol (180 litre) to give the corresponding crude extracts in 204.2, 192.7 and 1187.0 gm, respectively. The crude methanol extract was further partitioned with ethyl acetate(12 litre)-water(4.35 litre) and n-butanol(10 litre)-water to give ethyl acetate, n-butanol and water fractions in 103.6, 388.7 and 401.8 gm, respectively.

The ethyl acetate fraction (100 gm) was chromatographed on silica gel (Merck no. 7734, 1.62 kg, the extract was premixed with 180 g of the silica gel), eluting with mixtures of hexane-ethyl acetate and ethyl acetate-methanol. Fractions (300 ml, each) were combined on the basis of TLC to give a total of 19 fractions ($F_1$ to $F_{19}$). Fractions $F_7$ (1.10 g)

and F₈ (0.84 gm) eluting with 7–8% ethyl acetate-hexane, were repeatedly chromatographed on silica gel employing hexane-ethyl acetate as eluting solvents. The fraction eluted with 30% ethyl acetate-hexane gave a light yellow solid which was further purified by radial chromatography (silica gel, 20% ethyl acetate-hexane) and recrystallization from methylene chloride-methanol to give VR-3016 (0.2373 gm). The mother liquor was purified by HPLC (methylene chloride), followed recrystallization in the same solvent to give additional 0.1103 g of VR-3016. The compound has been identified as a new modified xanthone derivative, which has been given the name sootepenseone 1, on the basis of spectral data and single crystal x-ray diffraction analysis.

Physico-chemical data of sootepenseone (1):

m.p. 192–193° C. $[\alpha]^{28}D$–8.00, c=0.075 in $CHCl_3$ Elemental analysis: Found: C,72.32; H, 6.89. $C_{28}H_{32}O_6$ requires: C,72.39, H, 6.94. IR, $\lambda_{max}$ $CHCl_3$ cm$^{-1}$: 3560, 3033, 3011, 2980, 2932, 1740, 1638, 1590, 1470, 1428, 1382. UV, $\lambda_{max}$ EtOH nm (log e): 213(3.06), 263(2.18), 326(sh) (2.66), 355(2.74). Mass Spectrum: m/z (70eV) 464(2%), 436(100), 421(45), 367(17), 339(60), 297(40), 281(8), 241 (7), 215(28), 69(90).

NMR assignments: $^1H$ and $^{13}C$ NMR (300 and 400 Mhz, $CDCl_3$): see separate page The described isolation procedure is summarized in scheme 1.

Characterization of the Structure of Sootepenseone (1)

The identity of sootepenseone was revealed by analysis of its spectral data i.e. the infrared spectrum, ultraviolet spectrum, mass spectrum and particularly the $^1H$ n.m.r and $^{13}C$ n.m.r spectra.

TABLE 1

$^1H$-n.m.r. data of sootepensone (1) (δ Units, multiplicities)

| Protons and assignments | Sootepenseone (1) | long range $^1H$-$^{13}C$-correlation (correlated C-atoms) |
|---|---|---|
| C2-H | 6.05 (s) | C1, C4, C9a |
| C7-H | 3.42 (dd) | C6, C8a, C5*, C2" |
| C8-H | 7.50 (d) | C4b, C6, C7 |
| C1'-H | 1.40 (d) | C2', C3' |
| C2'-H | 4.40 (g) | — |
| C4'-H | 1.18 (s) | C2', C3', C4' |
| C5'-H | 1.60 (s) | C2', C3', C4' |
| C1"-CH2 | 2.27 (dd) | — |
| C1"-CH2 | 1.37 (dd) | — |
| C2"-H | 2.45 (d) | C4b, C8a, C1", C3" |
| C4"-H | 1.28 (s) | C2", C3" |
| C5"-H | 1.73 (s) | C2", C3" |
| C1'''-CH2 | 2.58 (bd) | C4b, C5, C3''', C4''' |
| C1'''-CH2 | 2.50 (dd) | C4b |
| C2'''-H | 4.40 (m) | — |
| C4'''-H | 1.37 (dd) | C2''', C3''' |
| C5'''-H | 1.10 (dd) | C2''', C3''' |
| C1-OH | 13.10 (s) | C1, C2, C9a |

*: suggested correlation

TABLE 2

$^{13}C$-n.m.r. data of sootepensone (1) (δ Units, multiplicities)

| C-atoms and assignments | Sootepenseone (1) |
|---|---|
| C1 | 166.2 (s) |
| C2 | 92.6 (s) |
| C3 | 168.5 (s) |
| C4 | 113.6 (d) |
| C4a | 156.0 (s) |
| C4b | 90.9 (s) |
| C5 | 84.6 (s) |
| C6 | 203.6 (s) |
| C7 | 47.1 (d) |
| C8 | 134.1 (d) |
| C8a | 133.7 (s) |
| C9 | 178.9 (s) |
| C9a | 101.4 (s) |
| C1' | 13.5 (q) |
| C2' | 91.0 (d) |
| C3' | 43.2 (s) |
| C4' | 21.0 (q) |
| C5' | 23.9 (q) |
| C1" | 26.0 (t) |
| C2" | 49.6 (d) |
| C3" | 82.9 (s) |
| C4" | 28.9 (q) |
| C5" | 30.7 (q) |
| C1''' | 29.0 (t) |
| C2''' | 117.8 (d) |
| C3''' | 135.3 (s) |
| C4''' | 25.5 (q) |
| C5''' | 16.9 (q) |

Relative Stereochemistry

The relative stereochemistry of sootepenseone (1) has been confirmed by single crystal x-ray diffraction analysis. Hence the absolute configuration is either the stereochemistry as depicted below

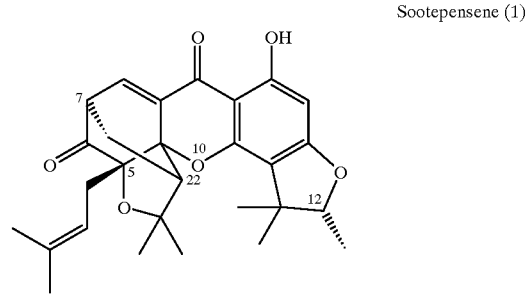

Sootepensene (1)

or the corresponding enantiomeric form thereof. The relative stereochemistry as depicted above for sootepenseone (1) is also valid for the sootepenseone derivatives according to formula (I), except for those derivatives where inversion or racemization occured under the selected reaction conditions at one or more of the chiral centers at C-5, C-7, C-10a, C-12 and C-22.

Preparation of Derivatives of Sootepenseone

TABLE 3

(I)

[Chemical structure of compound I with numbered positions 1-22, showing R¹, R², R³ substituents and various methyl groups]

| Compound No. | R¹ | R² | R³ |
|---|---|---|---|
| 1 (Sootepenseone) | H | \multicolumn{2}{l}{R2 and R3 forming part of the $C^{17}$—$C^{18}$ double bond} | |
| 6 | acetyl | R2 and R3 forming part of the $C^{17}$—$C^{18}$ double bond | |
| 7 | a pharmaceutically acceptable counter ion* | R2 and R3 forming part of the $C^{17}$—$C^{18}$ double bond | |
| 8 | $C_2$–$C_{20}$-alkyl-carbonyl | R2 and R3 forming part of the $C^{17}$—$C^{18}$ double bond | |
| 9 | methyl | R2 and R3 forming part of the $C^{17}$—$C^{18}$ double bond | |
| 10 | $C_2$–$C_{20}$-alkyl | R2 and R3 forming part of the $C^{17}$—$C^{18}$ double bond | |
| 11 | benzoyl | R2 and R3 forming part of the $C^{17}$—$C^{18}$ double bond | |
| 12 | benzoyl substituted with —OH or —OCH$_3$ | R2 and R3 forming part of the $C^{17}$—$C^{18}$ double bond | |
| 13 | H | H | H |

*suitable counter cations for the phenolat anion are, for example, Na+, K+, ½ Mg++, ½ Ca++, HN($C_{1-6}$-alkyl)$_3$+

Preparation of the compounds 6 to 13 can be accomplished starting from sootepenseone (1) by organic chemistry standard derivatization procedures which are well-known to the person skilled in the art.

EXAMPLE 2

Preparation of 1-O-Acetyl-sootepenseone (6)

A solution of 1 mg of sootepensione (1) in 1 ml anhydrous acetic acid anhydride was stirred at room temperature for 1 h. The solvent was evaporated in a water bath under reduced pressure. Yield: 1 mg of (6) as a crude residue.

For example, salts of sootepenseone (7) can be prepared according to methods and reagents as described in Houben-Weyl, Methoden der Organischen Chemie (methods in organic chemistry), 4th edition 1963, volume 6/2, "Sauerstoffverbindungen I (oxygen compounds I), part 2", pages 35 ff. So, for example, one eqivalent of a suitable base can be reacted with one equivalent of sootepenseone in a suitable solvent and then evaporating off the solvent or filtrating off the precipitated salt (7). A suitable base, for example, can be selected from the group consisting of alkali or earth alkali hydroxides or an organic amine.

Methylation of the OH-group (compound no. 9) can be accomplished starting from sootepenseone (1) with diazomethan in analogy to the method as described by Mustafa; Hishmat; JOCEAH; J.Org.Chem.; 22; 1957; 1644, 1646.

Acylation of the OH-group (compounds no. 6, 8, 11 and 12) can be accomplished starting from sootepenseone (1) in analogy to the method and reagents as described in Houben-Weyl, Methoden der Organischen Chemie (methods in organic chemistry), 4th edition 1985, volume E5, "Carbonsäuren und Carbonsäure-Derivate (carboxyclic acids and their derivatives)", pages 691 ff. Alkylation of the OH-group at C-1 (compound no. 10) can be accomplished starting from sootepenseone (1) in analogy to the standard procedures and by using standard reagents as described in Houben-Weyl, Methoden der Organischen Chemie (methods in organic chemistry), 4th edition, volume VI/3, "Sauerstoffverbindungen (oxygen compounds), part 3", Georg Thieme Verlag Stuttgart, 1965, pages 49 ff.

Hydrogenation of the isoprenyl $C^{17}$-$C^{18}$ double bound to the $C^{17}$—$C^{17}$ single bound (wherein $R^2$ and $R^3$ in the formula (I) are each a hydrogen atom; compound no. 13) can be performed by standard procedures as described for example in Houben-Weyl, Methoden der Organischen Chemie (methods in organic chemistry), 4th edition, volume IV/1c, "Reduktion (reduction), part 1", Georg Thieme Verlag Stuttgart, 1981, pages 15 ff.

Biological Activity

The compound according to the invention are less toxic than the standard compounds (see table 1). On the other hand, sootepenseone (1; D-25637) is more active in the hollow-fiber test as the standard compounds (see table 3).

TABLE 1

Toxicity of sootepenseone (D-25637)

| Compound | LD50 (mg/kg i.p. mice) |
|---|---|
| Sootepenseone (1; D-25637) | >100 |
| Actinomycin D | ca. 1 |
| Vinblastin | ca. 6 |
| Adriamycin | ca. 40 |
| Bleomycin | ca. 80 | i.p. intraperitoneal

Discussion of the Results:

Sootepenseone is at least 100 times less toxic than Actinomycin D, about 16 times less toxic than Vinblastin, and 60% and 20% less toxic than Adriamycin resp. Bleomycin.

2. In Vitro Antitumor Activity (XTT proliferation/cytotoxicity test)

The XTT-assay was carried out as described by D. A. Scudiero et al., Cancer Res. 48 (Sep. 1, 1988), pp. 4827–4833. The results of this procedure are expressed as that dose which inhibits growth by 50% as compared to control growth after 45 hours following application of the substance. The dose value as obtained is referred to as ED 50 and activity is indicated for ED 50 levels of $\leq 30$ μg/ml. The smaller the ED 50 level, the more active is the test material. The activities of sootepenseone (1) obtained in Example 1 are reported below in Table 2.

TABLE 2

| Compound | Cell line | ED 50 µg/ml |
|---|---|---|
| Sootepenseone (1; D-25637) | KB | 1.74 |
| | L1210 | 1.74 |
| | SK-OV-3 | 1.74 |
| | LNCAP | 1.74 |
| Actinomycin D | KB | 0.17 |
| | L1210 | 0.17 |
| | SK-OV-3 | 1.74 |
| | LNCAP | 0.17 |
| Adriamycin | KB | 0.17 |
| | L1210 | 0.017 |
| | SK-OV-3 | 0.17 |
| | LNCAP | 0.17 |
| Bleomycin | KB | 0.17 |
| | L1210 | 0.017 |
| | SK-OV-3 | 0.17 |
| | LNCAP | 0.17 |

TABLE 2-continued

| Compound | Cell line | ED 50 µg/ml |
|---|---|---|
| Vinblastin | KB | 0.17 |
| | L1210 | 0.017 |
| | SK-OV-3 | 0.17 |
| | LNCAP | 0.17 |

KB: epidermal carcinoma of the oral cavity
L1210: mice lymphatic leukemia
LNCaP: lymphoma metastasis of prostate carcinoma
SK-OV-3: human ovarian carcinoma
MCF-7: human breast cancer Discussion of the Results:

D-25637 has a significant anticancer activity against all tested tumor cell lines.

3. In vivo antitumor activity of sootepenseone (D-25637) (hollow fiber assay)

The hollow-fiber test was carried out as described by Melinda G. Hollingshead et al. in Life Sciences, Vol. 57, No. 2, pp.131–141, 1995. The results are shown in table 3.

TABLE 3

| Compound | Dose (mg/kg) | Location | % Inhibition (cell line) KB | % Inhibition (cell line) MCF-7 |
|---|---|---|---|---|
| Sootepenseone (1; D-25637) | 4 × 10 i.p. | s.c. | 49 | 41 |
| Actinomycin D | 4 × 0.1 i.p. | s.c. | 40 | −150 |
| Adriamycin | 4 × 4 i.p. | s.c. | 52 | 41 |
| Bleomycin | 4 × 8 i.p. | s.c. | 53 | −67 |
| Vinblastin | 4 × 0.65 i.p. | s.c. | 13 | −165 |

KB: epidermal carcinoma of the oral cavity
MCF-7: human breast cancer
s.c. subcutaneous
i.p. intraperitoneal Discussion of the Results:

D-25637 is more active (49% inhibition) against the KB tumor cell line than Vinblastin (13%) and Actinomycin D (40%), and nearly as active as Bleomycin (53%). Moreover, against the MCF-7 cell line D-25637 showed an as strong anticancer activity (41%) as adriamycin, while Actinomycin D, Bleomycin and Vinblastin enhanced tumor growth (negative inhibition values indicate increase in cell growth compared to untreated control group).

Scheme 1

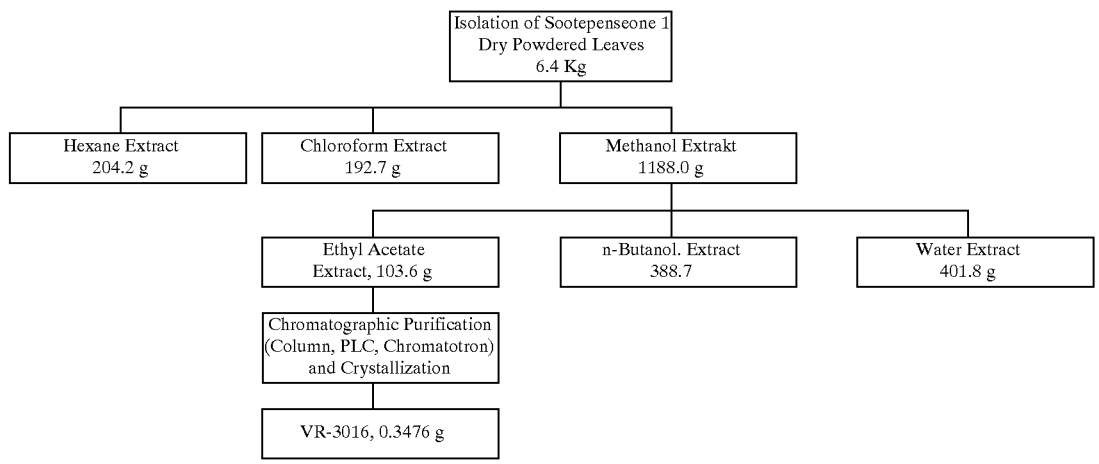

What is claimed is:

1. A compound according to general formula I

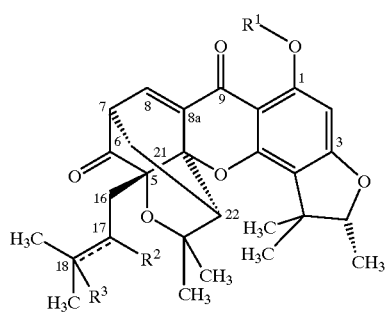

(I)

wherein $R^1$ is a hydrogen atom; a methyl group (—CH$_3$), a C$_2$–C$_6$ alkyl group, a formyl group (—CHO); an acetyl group (—COCH$_3$), —CO—C$_{2-6}$-alkyl, CO—C$_{3-8}$-cycloalkyl, —CO—$C_{6-18}$-aryl or —CO—$C_{7-24}$-aralkyl group each having optionally one or more substituents selected from the group consisting of —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —$NHCOR^2$, —$NO_2$, —CN, —(CO)$R^3$, —(CS)$R^4$, —F, —CI, —Br, —I, —O—$C_{1-6}$-alkyl, —O—$C_{6-14}$-aryl, —O—(CO)$R^5$, —S—$C_{1-6}$-alkyl, —S—$C_{6-14}$-aryl, —$SOR^6$, and —$SO2R^7$, wherein $R^2$ to $R^7$ stands independently of each other for a hydrogen atom, —$C_{1-6}$-alkyl, —O—$C_{1-6}$-alkyl, —O—$C_{6-14}$-aryl, —NH2, —$NHC_{1-6}$-alkyl, —$N(C_{1-6}$-alkyl$)_2$, —$NHC_{6-14}$-aryl, —$N(C_{6-14}$aryl$)_2$, —$N(C_{1-6}$-aryl$)(C_{6-14}$-alkyl$)$, —S—$C_{1-6}$alkyl, —S—$C_{6-14}$-aryl group;

a —COO—$C_{1-6}$-alkyl group having optionally one or more subsrituents selected from the group consisting of —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —$NHCOR^8$, —$NO_2$, —CN, —(CO)$R^9$, —(CS)$R^{10}$, —F, —CI, —Br, —I, —O—$C_{1-6}$-alkyl, —O—$C_{6-14}$-aryl, —O—(CO)$R^{11}$, —S—$C_{1-6}$-alkyl, —S—$C_{6-14}$-aryl, —$SOR^{12}$, and —$SO2R^{13}$, wherein $R^8$ to $R^{13}$ stands independently of each other for a hydrogen atom, —$C_{1-6}$-akyl, —O—$C_{1-6}$-alkyl, —O—$C_{6-14}$-alkyl, —NH2, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —S—$C_{1-6}$-alkyl, —S—$C_{6-14}$-aryl group;

a —$CONR^{14}R^{15}$ group wherein $R^{14}$ and $R^{15}$ stands independently of each other for a hydrogen atom, —$C_{1-6}$-alkyl, —O—$C_{1-6}$-alkyl, —O—$C_{6-14}$-aryl, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —S—$C_{1-6}$-alkyl, —S—$C_{6-14}$-aryl group;

or a counter cation selected from the group consisting of alkali metal ions, earth alkali metal ions, and $NR^{16}R^{17}R^{18}R^{19}(+)$ wherein $R^{16}$ to $R^{19}$ stands independently of each other for a hydrogen atom or a $C_1$–$C_6$-alkyl group;

$R^2$ and $R^3$ either form part of the $C^{17}=C^{18}$-double bond or are each hydrogen, or a tautomer, an enantiomer or a stereoisomer thereof or a physiologically acceptable salt or solvate thereof or mixtures thereof.

2. Compound according to formula I of claim 1, wherein $R^1$ is a hydrogen atom and $R^2$ and $R^3$ form part of the $C^{17}=C^{18}$-double bond.

3. A process for manufacturing a compound according to formula I of claim 1 or claim 2, wherein $R^1$ is a hydrogen atom and $R^2$ and $R^3$ form part of the $C^{17}=C^{18}$ double bond, comprising:

(a) extracting leaves of *Dasymaschalon sootepenseone* Graib, Annonaceae successively with organic solvents in an order of increasing polarity, (b) partitioning the crude extract of the highest polarity with a mixture of water and slightly miscible polar organic solvent, (c) purifying the organic extract by chromatography with suitable solvents, (d) optionally repeating step c) with fractions containing sootepenseone, and (e) optionally purifying by recrystallization.

4. A process for the manufacture of a compound according to formula I of claim 1, wherein $R^1$ is a counter cation selected from the group consisting of alkali metal ions, earth alkali metal ions, and $NR^{16}R^{17}R^{18}R^{19}(+)$, wherein $R^{16}$ to $R^{19}$ stands independently of each other for a hydrogen atom or a $C_1$–$C_6$-alkyl group, a hydrogen atom, and $R^2$ and $R^3$ form part of the $C^{17}=C^{18}$ double bond, comprising reacting a compound according to formula I of claim 1, wherein $R^1$ is a hydrogen anion, with at least one equivalent of a suitable inorganic or organic base to obtain the corresponding phenolate salt.

5. A process for the manufacture of a compound according to formula I of claim 1, wherein $R^1$ has the meaning as defined in claim 1 and wherein $R^2$ and $R^3$ are each a hydrogen atom, comprising reacting a compound according to claim 1 with hydrogen, wherein $R^1$ has The meaning as defined in claim 1, and wherein $R^2$ and $R^3$ form part of the $C^{17}=C^{18}$ double bond.

6. A process for the manufacture of a compound according to formula I of claim 1, wherein $R^1$ is a methyl group (—$CH_3$), a $C_2$–$C_6$ alkyl group, a formyl group (—CHO);

an acetyl group (—$COCH_3$), —CO—$C_{2-6}$-alkyl, CO—$C_{3-8}$-cycloalkyl, —CO—$C_{6-18}$-aryl or —CO—$C_{7-24}$-aralkyl group each having optionally one or more substituents selected from the group consisting of —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —$NHCOR^2$, —$NO_2$, —CN, —(CO)$R^3$, —(CS)$R^4$, —F, —CI, —Br, —I, —O—$C_{1-6}$-alkyl, —O—$C_{6-14}$-aryl, —O—(CO)$R^5$, —S—$C_{1-6}$-alkyl, —S—$C_{6-14}$-aryl, —$SOR^6$, and —$SO2R^7$, wherein $R^2$ to $R^7$ stands independently of each other for a hydrogen atom, —$C_{1-6}$-alkyl, —O—$C_{1-6}$-alkyl, —O—$C_{6-14}$-aryl, —NH2, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —S—$C_{1-6}$-alkyl, —S—$C_{6-14}$-aryl group;

a —COO—$C_{1-6}$-alkyl group having optionally one or more substituents selected from the group consisting of —OH, —SH, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —$NHCOR^8$, —$NO_2$, —CN, —(CO)$R^9$, —(CS)$R^{10}$, —F, —CI, —Br, —I, —O-$C_{1-6}$-alkyl, —O—$C_{6-14}$-aryl, —O—(CO)$R^{11}$, —S—$C_{1-6}$-alkyl, —S—$C_{6-14}$-aryl, —SOR $^{12}$, and —$SO2R^{13}$, wherein $R^8$ to $R^{13}$ stands independently of each other for a hydrogen atom, —$C_{1-6}$-alkyl, —O—$C_{1-6}$-alkyl, —O—$C_{6-14}$-aryl, —NH2, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —S—$C_{1-6}$-alkyl, —S—$C_{6-14}$-aryl group;

a —$CONR^{14}R^{15}$ group wherein $R^{14}$ and $R^{15}$ stands independently of each other for a hydrogen atom, —$C_{1-6}$-alkyl, —O—$C_{1-6}$-alkyl, —O—$C_{6-14}$-aryl, —NH2, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)(C_{6-14}$-aryl$)$, —S—$C_{1-6}$-alkyl, —S—$C_{6-14}$-aryl group and wherein $R^2$ and $R^3$ either form part of the $C^{17}=C^{18}$-double bond or are each a hydrogen atom, comprising reacting a compound according to claim 1, wherein $R^1$ is a hydrogen atom or a counter cation selected from the group consisting of alkali metal ions, earth alkali metal ions, and $NR^{16}R^{17}R^{18}R^{19}(+)$ wherein $R^{16}$ to $R^{19}$ stand independently of each other for a hydrogen atom or a $C_1$–$C_6$-alkyl residue, with a suitable alkylating or acylating reagent in the presence or absence of a base.

7. A pharmaceutical composition comprising at least one compound according to formula I of claim 1 or claim 2, optionally together with one or more components selected from the group consisting of physiologically acceptable carriers, diluents and excipients.

8. A process for manufacturing a pharmaceutical composition comprising processing one or more compounds according to formula I of claim 1, optionally together with one or more components selected from the group consisting of physiologically acceptable carriers, diluents, and excipients, into an appropriate pharmaceutical form.

9. A method of treating a tumor comprising administering an effective dose of at least one compound according to formula I of claim 1 or claim 2 to a human or animal patient in need thereof, wherein the tumor is selected from the group consisting of adrenocarcinomas, glioblastomas, breast tumors, cervical tumors, colorectal tumors, endometrial tumors, gastric tumors, liver tumors, small cell lung tumors, non-small cell lung tumors, lymphomas, metastatic melanomas, neuroblastomas, osteogenic sarcomas, ovarian tumors, retinoblastoma, soft tissue sarcomas, and testicular tumors.

10. A method of manufacturing a pharmaceutical composition comprising combining a compound according to claim 2 with at least one physiologically acceptable carrier, diluent, or excipient.

* * * * *